(12) United States Patent
Ellman et al.

(10) Patent No.: US 7,951,146 B2
(45) Date of Patent: May 31, 2011

(54) RF INTERVERTEBRAL ELECTROSURGICAL PROBE

(75) Inventors: Alan G. Ellman, Oceanside, NY (US); Jon C. Garito, Oceanside, NY (US)

(73) Assignee: Elliquence, LLC, Oceanside, NY (US)

( * ) Notice: Subject to any disclaimer, the term of this patent is extended or adjusted under 35 U.S.C. 154(b) by 1051 days.

(21) Appl. No.: 11/803,111

(22) Filed: May 14, 2007

(65) Prior Publication Data

US 2008/0287947 A1    Nov. 20, 2008

(51) Int. Cl.
*A61B 18/14* (2006.01)

(52) U.S. Cl. .................. 606/45; 606/46; 606/49

(58) Field of Classification Search ........... 606/41, 606/45–47, 49; 604/35
See application file for complete search history.

(56) References Cited

U.S. PATENT DOCUMENTS

| | | | | |
|---|---|---|---|---|
| 5,836,909 A * | 11/1998 | Cosmescu | | 604/35 |
| 6,159,209 A * | 12/2000 | Hakky | | 606/45 |
| 6,755,826 B2 * | 6/2004 | Valencic et al. | | 606/46 |
| 7,241,293 B2 * | 7/2007 | Davison | | 606/41 |
| 2006/0095034 A1 * | 5/2006 | Garito et al. | | 606/45 |

* cited by examiner

*Primary Examiner* — Lee S Cohen

(57) ABSTRACT

An electrosurgical instrument for spinal procedures comprises an elongated tubular member configured to fit within and be extended down a standard sized cannula. The instrument comprises a proximal end including a handle for the surgeon and supplied with fittings for connection to a source of irrigation fluid and a source of suction. The distal end of the instrument has an active end comprising a slightly-flexible curved wire electrode that extends in the plane of the tubular member. Beyond the wire electrode is an exit port for irrigation fluid, and in front of the electrode is a receiving port for suction. The wire electrode is thus flanked in front by the exiting irrigation fluid and behind by the suction, with the result that fluid flow is drawn by the suction across the wire electrode creating pressure forces that direct removed tissue to the suction entrance and its removal from the surgical site.

8 Claims, 2 Drawing Sheets

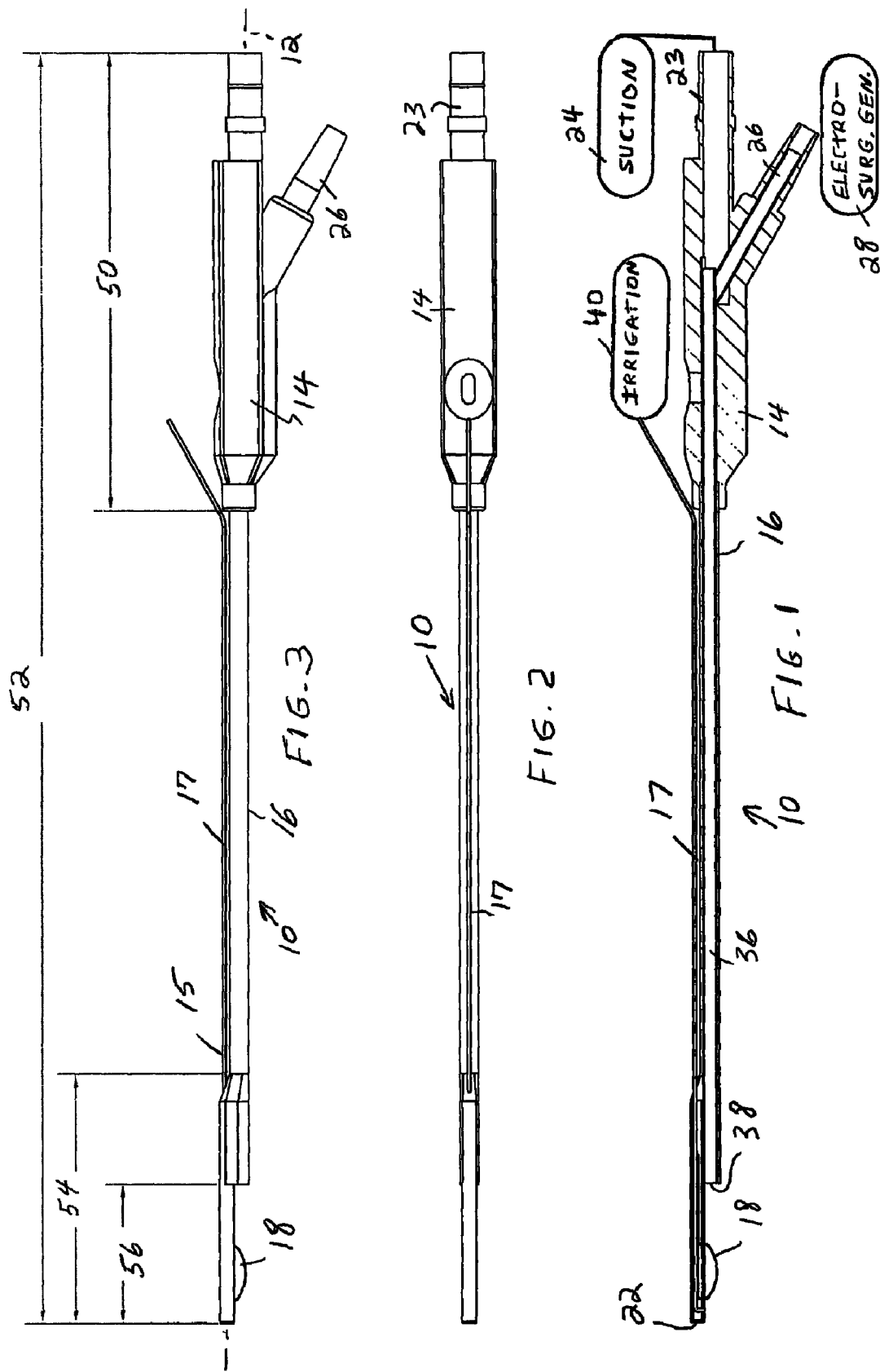

RF INTERVERTEBRAL ELECTROSURGICAL PROBE

This invention relates to an electrosurgical electrode for spinal and other surgical procedures.

BACKGROUND OF THE INVENTION

Our earlier U.S. Pat. No. 7,137,982, the contents of which are herein incorporated by reference, describes an electrosurgical instrument for spinal procedures comprising a generally scoop-shaped cup whose periphery is electrically active and is capable of applying RF electrosurgical currents to spinal tissue. The active electrode may comprise an exposed bare wire at the leading edge of the cup. A conduit in a handle section can convey suction to the cup. A tissue clearing member is pivotably mounted on or inside the cup and can be manipulated via a lever on the handle to help dislodge tissue. The tissue clearing member may be a radially-extending vane for rotation in the plane of the cup edge. The tissue clearing member may also be made electrically active thus selectively providing unipolar or bipolar operation. The surgeon can exercise control of tissue vaporization as the focused energy emitted from the scoop-shaped electrode is rapidly and locally absorbed and liquefies the cells.

While the patented device is suitable for many spinal procedures, there is a need in the art for an instrument that can electrosurgically remove tissue, and specifically disc nucleus pulposus, via a cannula for minimally invasive surgical (MIS) procedures.

SUMMARY OF THE INVENTION

An object of the invention is an improved surgical procedure for producing a void or cavity in human tissue.

Another object of the invention is an intervertebral electrosurgical electrode for forming a void in spinal tissue as part of a MIS procedure for replacing spinal tissue with an artificial disc prosthesis.

In accordance with one aspect of our invention, our novel instrument comprises an elongated tubular member configured to fit within and be extended down a standard sized cannula in a MIS procedure. The instrument comprises a proximal end including a handle for the surgeon and supplied with fittings for connection to a source of irrigation fluid and a source of suction. The distal end of the instrument has an active end comprising a slightly flexible curved wire electrode that extends in the plane of the tubular member. Beyond the wire electrode is an exit port for the irrigation fluid, and in front of the electrode is a receiving port for the suction. Thus, the wire electrode is flanked in front by the exiting irrigation fluid and behind by the suction, with the result that suction causes fluid flow across the wire electrode creating pressure forces that direct removed tissue to the suction entrance and its removal from the surgical site.

In accordance with another feature of the invention, the tubular member extends downstream beyond the irrigation port and also serves as a stop for use by the surgeon to position the wire electrode where desired.

In accordance with another feature of the invention, the far end of the tubular member is constructed of a radio-opaque material such that the instrument end is visible during fluoroscopic examination while the procedure is carried out.

The wire electrode is electrically active and is capable of applying electrosurgical currents to human tissue with the result that a void or cavity or tunnel can be formed in the tissue to a considerable depth. The tissue removed to form the cavity under pressure from the exiting irrigation fluid is then easily aspirated via the suction port.

A further feature of the invention is the use of radio-frequency (RF) electrosurgical currents, in a frequency range preferably above 3 MHz, with 4 MHz being preferred.

It is believed that 4 MHz radiofrequency energy has been proven to be a self-limiting, minimal penetration energy source capable of precise tissue interaction. Thus, electrosurgical instruments that emit 4 MHz radiofrequency currents will be attractive to spinal surgeons needing to produce a space-specific nucleotomy efficiently and safely. In combination with the innovative RF delivery system in a MIS procedure, radiofrequency energy can result in precision extraction of the nucleus pulposus and/or the entire disc that will enable a void to be created that will accommodate a replacement substance or device. Since lateral heat is typically not a byproduct of 4 MHz RF currents, damage to endplates can be minimized or avoided, nor will the RF currents violate the annulus.

Thus, a MIS electrosurgical procedure using the novel electrode described herein enables physicians to offer to patients a treatment that is efficiently performed, relatively easily learned and thus performed at a significantly reduced price, and with less tissue damage and superior results compared to procedures done with other voiding devices.

The electrosurgical procedure has the very important advantage of being able to excise spinal tissue portions while at the same time coagulating the cut tissue causing minimum bleeding. It is preferred that the electrosurgical currents be about 4 MHz. At these RF high frequencies, commonly referred to as radiosurgery, cutting is accomplished by volatilizing intracellular fluids at the point of the transmitting electrode contact which is primarily responsible for only small lateral heat spread and thus less damage to neighboring cell layers by keeping tissue temperature lower.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals or letters signifying the same or similar components.

BRIEF DESCRIPTION OF THE DRAWINGS

FIG. 1 is a side cross-sectional view of one form of intervertebral electrosurgical instrument of the invention shown schematically connected to electrosurgical apparatus, an irrigation source, and a suction generator;

FIG. 2 is a top view of the intervertebral electrosurgical instrument of FIG. 1;

FIG. 3 is a side view of the intervertebral electrosurgical instrument of FIG. 1 with dimensions added to assist in understanding the invention;

DETAILED DESCRIPTION OF THE PREFERRED EMBODIMENTS

Figure 4:
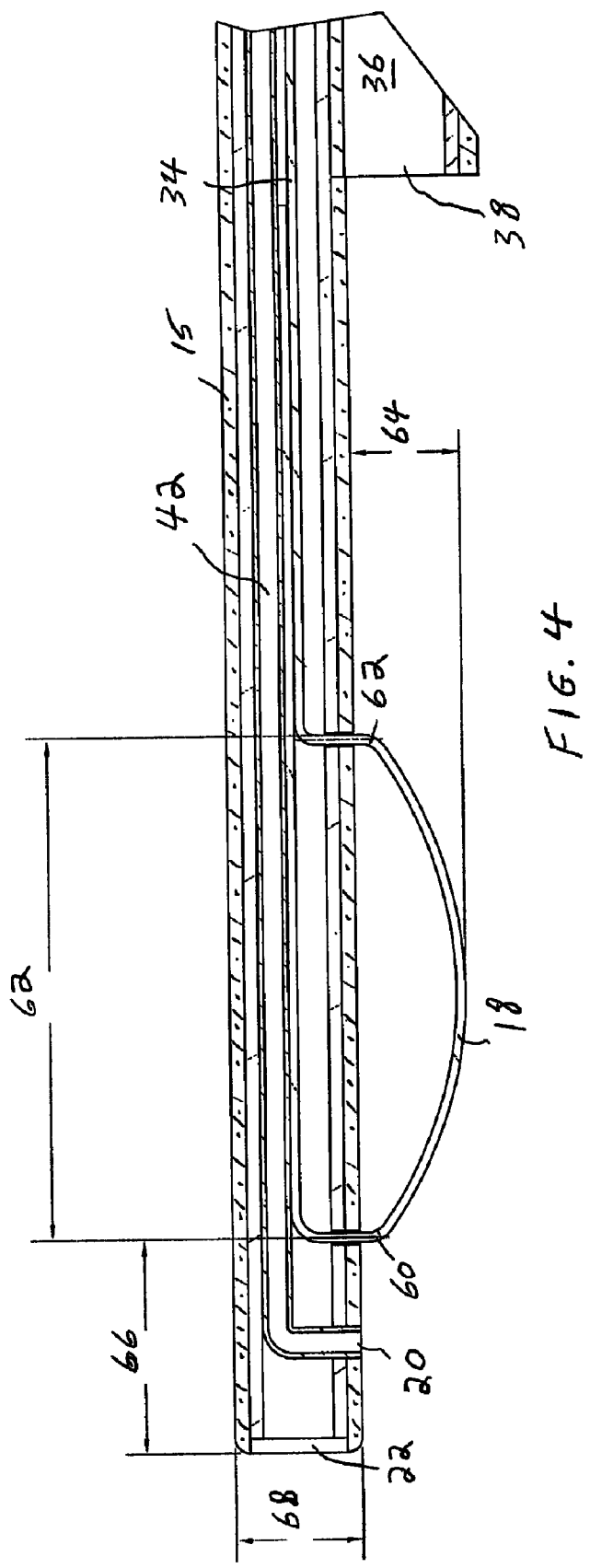
FIG. 4 is an enlarged cross-sectional view of the active working end of the intervertebral electrosurgical instrument of FIG. 1.

The novel design of the invention not only provides an active edge positioned for precise micro-cutting to remove well-defined segments of tissue exactly where the RF instrument is placed, but in addition the suction provided just inside of the active electrode simultaneously evacuates blood, tissue and RF plume from the surgical field for a clearer view. It is understood that the instrument in accordance with the invention is intended for use in MIS with a cannula with the instrument end being pushed down into the cannula until the working end protrudes free of the cannula for direct application to the tissue to be excised.

FIG. 1 illustrates a preferred form of the novel intervertebral electrosurgical instrument 10 of the invention. It comprises an elongated structure having a central axis 12 including at a proximate first end (at the right of FIG. 1) a handle 14 connected to an elongated tubular member 16 serving as a suction duct. Mounted on the tubular member 16 is a forwardly projecting member 15 including an irrigation duct 17 terminating at the opposite distal second end at a semi-elliptical wire electrode 18 extending below and in the same plane as that of the instrument 10. Extending just past the wire electrode distal end is the exiting port 20 (FIG. 3) for the irrigation duct 17. Extending beyond the wire electrode 18 and the irrigation port 20 is a plate-like member 22 that closes off the tubular member 15. At the first end of the tubular member 16 is mounted a fitting 23 for receiving a conduit (not shown) connected in turn to a conventional suction generator 24. At the same first end is mounted a female electrical connector 26 which is connected via a cable in the conventional manner directly or via an adaptor to the unipolar socket of conventional electrosurgical apparatus 28. As an example only, and not meant to be limiting, the electrosurgical apparatus 28 can be model AAOP Surgitron FFPF or the Dual-Frequency Unit available from the Ellman company of Oceanside, N.Y. The Ellman equipment is preferred due to its high operating frequency, typically at about 4 MHz.

The handle 14 and tubular member 16 including the irrigation duct 17 is a unitary body constructed of a suitable metal covered with an electrically-insulating material, or may be of a suitable electrically-insulated plastic such as ABS. The electrical connector 26 is electrically connected via an internal wire 34 to the wire electrode 18. The latter may be, for example, of tungsten or of stainless steel or another alloy, and dimensioned to be slightly flexible. For example, the wire diameter may be in the range of 0.007-0.020 inches. The slight flexibility is helpful because when the instrument is pushed down the cannula, the wire flexibility allows the wire to flatten to fit within the cannula, but upon emerging from the cannula end, the wire will spring back to its original semi-elliptical shape as illustrated in the drawings. When the electrosurgical unit 28 is activated, unipolar electrosurgical currents flow via the internal wire 34 to the wire electrode 18 and thence to any tissue in contact with the electrode.

The suction generator 24 is connected directly to a suction duct 36 (the interior of the tubular member 16) which runs the full length of the tubular member 16 and exits via a suction port 38 just before the wire electrode 18, on its near side 62. The irrigation source 40 in turn is connected directly to the irrigation duct 42 which runs the full length of and on the tubular member 16 and exits via the irrigation port 20 just beyond the wire electrode 18, on its far side 60. The suction when activated will cause the exiting irrigation fluid to flow across the wire electrode 18 toward and into the suction port 38 clearing the site of any vapors or liquids or excised tissue when the activated wire electrode excises the tissue contacted during a procedure. The location of the irrigation port 20 on the far side 60 of the wire electrode with the suction port 38 on the near side 62 of the wire electrode takes advantage of the fluid pressure created by the exiting irrigation fluid exposed to the suction force which tends to push any excised tissue toward the suction port where it can quickly be conveyed away from the surgical site.

The whole instrument 10 in use is typically made from electrically-insulating material or of metal covered by a plastic coating. Hence, during use, the entire assembly apart from the electrodes is shielded from the electrosurgical currents and thus prevented from inadvertently causing injury to the patient.

In order for the instrument of the invention to perform a MIS intervertebral procedure, certain dimensions of the instrument are important for the active end with the wire electrode to reach the desired spinal tissue and/or create a channel to reach interior tissue to be excised. In the preferred embodiment, with a handle length 50 about 3.75-4.5 inches, the overall length 52 of the instrument is about 11-14 inches, the length 54 is about 2.0-2.4 inches, and the dimension 56 is about 1.1-1.4 inches. The axial length 62 of the wire electrode from its far side 60 to its near side 62 is about 0.125-2 inches, preferably 0.5 inches, and its depth 64 is about 0.1-0.8 inches, preferably 0.11 inches. The suction channel 36 should have sufficient size to allow a reasonable negative pressure to exist at the surgical site. The suction port 38 is preferably about 0.5 inches from the near side 62 of the wire electrode, and the irrigation port 20 is about 0.1 inches downstream of the far side 60 of the wire electrode, which ensures a substantial fluid flow across the wire electrode.

The entire structure which constitutes a unipolar probe is stiff and sturdy and, apart from the wire electrode, does not flex during use. Also connected to the electrosurgical unit 32 is the usual indifferent plate which during use is in contact with the patient's body. When the electrosurgical apparatus 28, irrigation source 40, and suction generator 24 are energized, high frequency electrosurgical currents are generated which are coupled by way of the electrically conductive wire in the handle to the active wire loop 18. The physician, in the usual way, holds the handle 14 while applying the working wire electrode 18 of the probe to the desired area of the patient to be treated. Any excised tissue, smoke or blood is evacuated under the suction produced at the suction end 38 which is closely spaced to and thus effective at the surgical site. The electrosurgical currents simultaneously with the excising will coagulate any bleeders avoiding excessive blood and other fluids that may obstruct vision of the surgeon.

As will be noted, the tubular member 15 carrying the irrigation duct 17 extends downstream past the irrigation port 20. The surgeon, knowing the length of this extension, can use the end 22 as a stop to position the wire electrode where desired. Preferably, the end plate 22 extends (reference numeral 66) about 0.212 inches beyond the far end 60 of the wire electrode 18. This distance can vary between about 0.180-0.315 inches. The width 68 of the distal end is about 0.13 inches.

The plate 22 at the far end of the irrigation duct 17 preferably is constructed of a known radio-opaque material such that the instrument end is visible during fluoroscopic examination while the procedure is carried out.

While the instrument of the invention is especially useful for spinal procedures, it is not limited to such uses and it will be understood that it can be employed in any electrosurgical procedure employing a cannula in MIS.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument for excising of tissue, comprising:
   (a) an elongated handle portion having a longitudinal axis and comprising at a proximate end an electrical connector for receiving electrosurgical RF currents, a fluid fitting for receiving irrigation fluid, and a suction fitting for receiving suction,
   (b) a suction conduit on the handle portion and connected at one end to the suction fitting,
   (c) an irrigation conduit on the handle portion and connected at one end to the fluid fitting,
   (d) the handle portion having at a distal end a bare exposed wire-shaped electrode serving as the active electrode, the wire-shaped electrode extending in the plane of the handle portion and parallel to the longitudinal axis spaced laterally from the handle portion, the wire-shaped electrode having a near side closer to the proximate end of the handle portion and a far side closer to the distal end of the handle portion, the wire electrode being constituted of slightly flexible wire such that it will flatten when the instrument is forced down a cannula,
   (e) means on the handle for connecting the electrical connector to the active electrode,
   (f) the suction conduit having at the distal end a suction port positioned adjacent the near side of the wire electrode,
   (g) the irrigation conduit having at the distal end an irrigation port positioned adjacent the far side of the wire electrode,
   (h) the wire electrode extending down below the irrigation conduit and the suction port being positioned on the side of the handle portion with its opening facing the wire-shaped electrode and the distal end of the handle portion such that fluid exiting from the irrigation port is drawn by the suction force longitudinally along the wire electrode carrying with it any tissue excised by the electrode.

2. An electrosurgical instrument as claimed in claim 1, wherein the wire electrode has a semi-elliptical shape with its far side sloping toward the distal end and its near side sloping toward the proximate end to favor flattening during passage through the cannula.

3. An electrosurgical instrument as claimed in claim 1, wherein the near side of the wire electrode is spaced about 0.5 inches from the suction port.

4. An electrosurgical instrument as claimed in claim 1, wherein the far side of the wire electrode is spaced about 0.1 inches from the irrigation port.

5. An electrosurgical instrument as claimed in claim 1, wherein the wire electrode spacing from its far to its near side is about 0.5 inches.

6. The electrosurgical instrument as set forth in claim 1, wherein a portion of the handle portion extends beyond the far side of the wire-shaped electrode and is constituted of electrically-insulating material or of electrically-insulating-material-coated metal and serves as a stop for positioning the wire-shaped electrode.

7. The electrosurgical instrument of claim 1, in combination with:
   (a) electrosurgical apparatus capable of supplying high frequency electrosurgical currents to the electrical connector,
   (b) a suction generator for receiving the suction fitting,
   (c) an irrigation source for receiving the fluid fitting.

8. The combination of claim 7, wherein the high frequency currents are at a frequency of about 4 MHz.

* * * * *